(12) United States Patent
Despa et al.

(10) Patent No.: US 11,944,783 B2
(45) Date of Patent: Apr. 2, 2024

(54) ELECTRONIC MODULES FOR A SYRINGE

(71) Applicant: Becton, Dickinson and Company, Franklin Lakes, NJ (US)

(72) Inventors: Mircea Stefan Despa, Cary, NC (US); Adam Martin, Holly Springs, NC (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 153 days.

(21) Appl. No.: 16/761,483

(22) PCT Filed: Nov. 13, 2018

(86) PCT No.: PCT/US2018/060657
§ 371 (c)(1),
(2) Date: May 4, 2020

(87) PCT Pub. No.: WO2019/099355
PCT Pub. Date: May 23, 2019

(65) Prior Publication Data
US 2020/0289751 A1    Sep. 17, 2020

Related U.S. Application Data

(60) Provisional application No. 62/586,040, filed on Nov. 14, 2017.

(51) Int. Cl.
*A61M 5/172* (2006.01)
*A61M 5/31* (2006.01)
*A61M 5/32* (2006.01)

(52) U.S. Cl.
CPC .......... *A61M 5/172* (2013.01); *A61M 5/3137* (2013.01); *A61M 5/3243* (2013.01);
(Continued)

(58) Field of Classification Search
CPC .............................................. A61M 2205/332
See application file for complete search history.

(56) References Cited

U.S. PATENT DOCUMENTS 6,171,276 B1 * 1/2001 Lippe .................... A61M 5/20
128/DIG. 1
2005/0004514 A1 * 1/2005 Hochman ........... A61M 5/1456
604/67

(Continued)

FOREIGN PATENT DOCUMENTS

CN      110891634 A    3/2020
EP       3624876 A1    3/2020
(Continued)

OTHER PUBLICATIONS

International Search Report dated Feb. 28, 2019 issued in PCT/US2018/060657.
(Continued)

*Primary Examiner* — Emily L Schmidt
(74) *Attorney, Agent, or Firm* — Knobbe, Martens, Olson & Bear LLP

(57) ABSTRACT

An injection monitoring device includes a syringe having a barrel configured to contain a medicament and a plunger configured to be displaced linearly into the interior of the barrel to dispense the medicament, a flange positioned between a proximal end and a distal end of the injection monitoring device and configured to be gripped during performance of the injection, and one or more force sensors positioned to detect data associated with an amount of force applied to the injection monitoring device during performance of an injection.

24 Claims, 9 Drawing Sheets

(52) U.S. Cl.
CPC ............... *A61M 2005/3139* (2013.01); *A61M 2205/3317* (2013.01); *A61M 2205/332* (2013.01); *A61M 2205/3368* (2013.01); *A61M 2205/3584* (2013.01); *A61M 2205/52* (2013.01); *A61M 2205/702* (2013.01); *A61M 2205/8206* (2013.01)

(56) References Cited

U.S. PATENT DOCUMENTS

| | | |
|---|---|---|
| 2005/0252303 A1* | 11/2005 | Taniguchi ............... G01L 1/142 73/780 |
| 2008/0015406 A1 | 1/2008 | Dlugos |
| 2011/0144486 A1 | 6/2011 | Bruce |
| 2014/0288408 A1 | 9/2014 | Deutsch |
| 2016/0030683 A1 | 2/2016 | Taylor |
| 2016/0213856 A1 | 7/2016 | Despa |
| 2016/0259913 A1 | 9/2016 | Ning et al. |
| 2017/0136185 A1* | 5/2017 | Rios ................... A61M 5/31511 |
| 2018/0211562 A1* | 7/2018 | Rios ........................ G09B 23/30 |
| 2018/0333543 A1* | 11/2018 | Diaz .................... A61M 5/3202 |
| 2020/0093993 A1* | 3/2020 | O'Rourke ........... A61M 5/3158 |

FOREIGN PATENT DOCUMENTS

| | | |
|---|---|---|
| WO | WO 2015/136564 A1 | 9/2015 |
| WO | WO 2018/213837 | 11/2018 |
| WO | WO 2018/213837 A1 | 11/2018 |

OTHER PUBLICATIONS

Extended European Search Report, dated Jul. 14, 2021, issued in Co-pending EP Application No. 18880029.6.

* cited by examiner

ELECTRONIC MODULES FOR A SYRINGE

RELATED U.S. APPLICATIONS

This application is a U.S. national phase application of International Application No. PCT/US2018/060657, filed Nov. 13, 2018, which claims priority to U.S. Provisional Appl. No. 62/586,040 filed on Nov. 14, 2017, which is hereby incorporated by reference in its entirety.

BACKGROUND

Field

The invention relates to syringes, and more particularly, relates to smart devices for capturing dosing data from syringes.

Description of the Related Art

There are many diseases wherein patients have an active role in disease management. Under some treatment regimens, patients may be required to inject medicament into their body multiple times per day. For example, diabetic patients must self-inject insulin in order to control blood sugar levels.

When preparing to self-inject a medicament, a patient may need to take several factors into account. For example, the patient may need to keep track of previous injection dose amounts as well as the precise times at which those doses were administered to calculate the dose amount and time for a subsequent self-injection. The patient may need to inject the medicament several times a day at varying levels. The patient may find it difficult to keep track of the dose amount and time of each injection event. These issues create a possibility of errors occurring in the patient's determined dose amounts and times which are used for subsequent self-injections. Patients may also fail to completely empty a syringe when performing an injection. This may result in the improper dosage of a medicament being administered to the patient. The injection of improper dosages may result in poorer clinical outcomes.

SUMMARY

Aspects of the invention include systems, devices, and methods for monitoring dosing data.

One embodiment is an electronic injection monitoring device configured to mate with a syringe having a flange. The electronic monitoring device includes a channel configured to receive at least a portion of the syringe, one or more flange members configured to couple to the flange of the syringe and to be gripped during performance of an injection, one or more force sensors positioned connected to the flange members, and a communication module configured to transmit data from the force sensors to an external device.

Another embodiment is an electronic injection monitoring device configured to mate with a syringe having a plunger. The electronic monitoring device includes a body configured to mate with a proximal end of the syringe plunger, one or more force sensors positioned within an interior portion of the body, and a communication module configured to transmit data to an external device from the one or more force sensors.

Another embodiment is an electronic injection monitoring system. The electronic injection monitoring system includes a syringe having a barrel configured to contain a medicament and a plunger configured to be displaced linearly into the interior of the barrel to dispense the medicament. The plunger includes a finger press, a stopper, and a plunger rod extending between the finger press and the stopper. The electronic injection monitoring system further includes a flange positioned between a proximal end and a distal end of the injection monitoring device and configured to be gripped during performance of the injection, and one or more force sensors positioned to detect data associated with an amount of force applied to the injection monitoring device during performance of an injection.

Another embodiment is a method for monitoring progress of an injection of a medicament. The method includes providing a syringe configured to administer the medicament and an injection monitoring device including one or more force sensors positioned to detect data associated with an amount of force applied to the syringe during performance of an injection of the medicament, detecting data from the one or more force sensors, and determining a state of the syringe based at least in part on the detected data.

DETAILED DESCRIPTION

Figure 1:
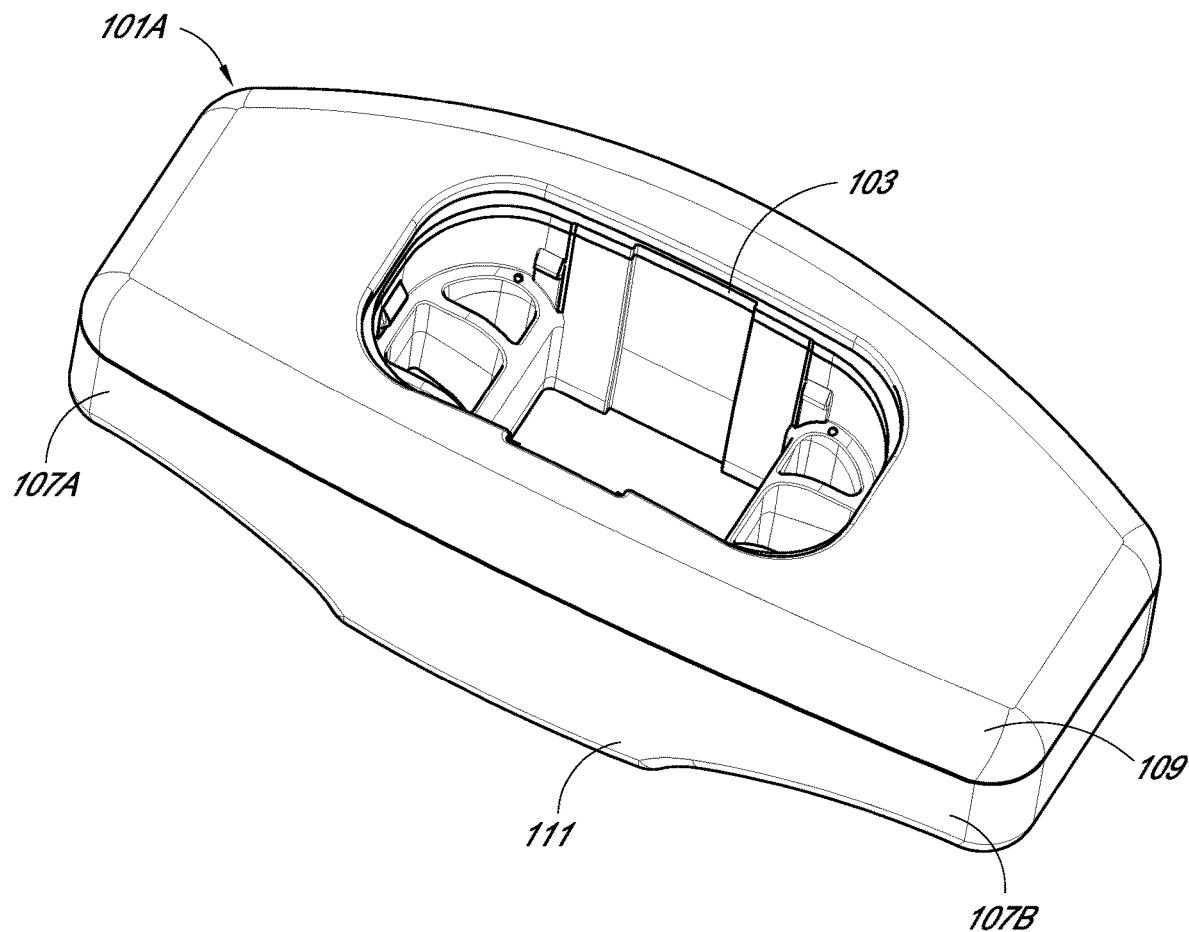
FIG. 1 depicts a perspective view of an injection monitoring device that attaches to a syringe flange in accordance with an illustrative embodiment of the present invention.

As will be appreciated by one skilled in the art, there are numerous ways of carrying out the examples, improvements, and arrangements of a medicament delivery device in accordance with embodiments of the invention disclosed herein. Although reference will be made to the illustrative embodiments depicted in the drawings and the following description, these embodiments are not meant to be exhaustive of the various alternative designs and embodiments that are encompassed by the disclosed invention. Those skilled in the art will readily appreciate that various modifications may be made, and various combinations can be made, without departing from the invention.

One embodiment is a medicament injection monitoring device that can be affixed to, or integrated with, a syringe, as depicted in FIGS. 1-6. In an illustrative embodiment, the injection monitoring device includes one or more sensors designed to fit within an interior space of a syringe, or be part of an adaptor or otherwise mate with the syringe. For example, in some embodiments, the injection monitoring device can include one or more sensors designed to fit within a flange and/or plunger of the syringe. In some embodiments, the injection monitoring device can include one or more modules that can be attached to and detached from the plunger or flange of a syringe. The one or more modules can house one or more sensors. For example, in one embodiment the injection monitoring device comprises an electronic removable flange configured to attach to a flange section of a syringe. The electronic removable flange can include one or more sensors that detect, track, store and report the operation of the syringe. In some embodiments, the removable flange can attach to a pre-existing flange of the syringe.

In this embodiment, the electronic flange module includes an upper surface and a lower surface. The lower surface may have one or more pressure sensors that sense the pressure of a user's fingers as an injection is being performed. For example, the user may press their thumb on the syringe's plunger, and two additional fingers against the lower surface of the electronic flange module. As the user squeezes the plunger to perform an injection, the upward force of their fingers along the lower surface of the electronic flange module will increase. As described below, capturing and measuring this force can be used to determine when an injection has occurred, how much medicine was injected, and whether the injection was completed, in addition to other data.

Another embodiment is an electronic finger press module that mates to the top of a syringe plunger. The electronic finger press module may include a pressure sensor on its upper surface that detects the pressure of a user's thumb or finger as injections are occurring. The downward pressure by the user as the injection is underway can be used to determine valuable data, as discussed herein below, that can be used to track and treat an individual receiving the injection.

In one illustrative embodiment, the injection monitoring device can include one or more sensors for detecting data relevant to movement of the syringe plunger by a user. For example, the movement may relate to an injection event, wherein the user is preparing for, or performing, an injection. The one or more sensors can include force sensors for detecting an external force, or load, applied to an exterior section of the injection device. In some embodiments, the force sensors can be oriented to detect one or more external forces associated with movement of the syringe plunger. For example, one or more force sensors can be oriented to detect an external force, or load, applied to the plunger and/or flange of the syringe during depression of the plunger within the syringe. Data from the force sensors can be processed to determine dosing status or event information, such as, for example, injection initiation, injection progress, injection completion, and amount of medicament injected.

In a typical injection using a syringe, several stepwise changes in actuating force exerted on the plunger or underside of the flange of the syringe can occur. A first change in force occurs upon initiation of an injection at which time the actuating force increases from zero to a first magnitude or first range of magnitudes. As fluid is dispensed from the syringe, the force required to move the plunger is relatively consistent. The applied force from the user on the syringe during dispensing of fluid can be maintained at the first magnitude or within the first range of magnitudes. When the fluid is emptied from the syringe, a stopper of the plunger contacts a bottom surface of a barrel of the syringe, preventing further movement of the plunger towards the needle, referred to herein as "bottoming out."

In normal use of the syringe, a second detectable change of force occurs during bottoming out of the stopper, which is accompanied by an increase in force exerted by the user from the first magnitude or first range of magnitudes to a second magnitude or second range of magnitudes greater than the first magnitude or first range of magnitudes. This may be due to a delay in the reaction of the user in recognizing that a full dose has been injected.

A third change in force occurs when the user removes his or her finger(s) from the plunger and/or underside of the flange. When one or more fingers are removed from the plunger and/or underside of the flange the actuating force decreases from the second magnitude or range of magnitudes to zero. The force sensors positioned within the plunger and flange can be positioned to detect one or more of the first change in force, second change in force, and third change in force. By measuring these forces, the injection monitoring device can determine the state of the injection process.

In an illustrative embodiment, the syringe can be a safety syringe. A safety syringe can include a safety shield or needle guard. In some embodiments, the safety shield or needle guard can be a BD UltraSafe Passive™ needle guard from Becton Dickinson® or a BD UltraSafe Plus™ passive needle guard from Becton Dickinson®. The injection monitoring device can include one or more sensors for detecting deployment of a safety shield. In some embodiments, deployment of the safety shield can be detected using one or more force sensors. In some embodiments, the injection monitoring device includes one or more switches positioned to be activated in response to deployment of the safety shield.

The injection monitoring device can also include one or more orientation sensors for determining the orientation of the syringe and for detecting sudden motions associated with syringe handling. The orientation sensors can be configured to detect motions of the syringe such as, but not limited to, sudden impacts associated with tapping on the side of the syringe. In some embodiments, different orientation sensors may be configured to determine orientations of the syringe to determine motions associated with syringe handling by the user. In an illustrative embodiment, the injection monitoring device can further include a digital clock or timer to record the time associated with any of the detected injection events, including motion of the plunger rod or stopper of the syringe.

In one embodiment, the injection monitoring device may further include a communication module for electronically connecting between the injection monitoring device and one or more external devices. The communication module can be connected to an external device using wired or wireless communication. This connection may be made using well-known wireless communication protocols, such as Bluetooth, WIFI, or other means. The injection monitoring device may further include a battery to provide power to the electrical components of the injection monitoring device.

The injection monitoring device may also be configured to transmit data from the sensors to an external device, such as a computer or mobile device. The external device may be configured to process the data to determine forces applied to the syringe are associated with an injection event. Data from the force sensors can also be processed to calculate the amount of medicament expelled from the syringe, i.e., the amount of dose injected into a user. The amount of dose and the time associated with an injection event can be recorded and displayed to a user on a user interface of the external device. The provided data can facilitate monitoring of adherence to a treatment plan. In some embodiments, the injection device can be a dose monitoring device that tracks or monitors the amount of a medicament that is administered to a subject.

During these operations, an orientation sensor within the injection monitoring device may be actively recording the orientation of the syringe for later analysis. This allows the system to process and more accurately predict when the actual dosing occurred based on the prior, and current, position of the syringe in three-dimensional space. For example, it's unlikely that force exerted on the plunger or underside of the plunger flange while the needle is facing up would be an injection event. Normally, an injection event would occur with the needle either facing downwards or approximately parallel with the ground.

In one embodiment, the syringe may be disposable but connected to an internal or external measurement device. In some embodiments, the injection monitoring device, or modules of such a device, including one or more sensors may be disposable as well. In other embodiments, one or more modules may be removed and attached to a different disposable syringe to convert it into an intelligent syringe that includes injection monitoring capabilities.

Although various persons, including, but not limited to, a patient or a healthcare professional, can operate or use illustrative embodiments of the present invention, for brevity an operator, patient or user will be referred to as a "user" hereinafter.

Although various fluids can be employed in illustrative embodiments of the present invention, fluid in a syringe will be referred to as "medicament" hereinafter.

FIG. 1 depicts an illustrative embodiment of an injection monitoring device 101A that is configured to mate with a syringe, such as, for example, a safety syringe. In some embodiments, the injection monitoring device 101A can be configured to interface with multiple syringes and with syringes of different types. The injection monitoring device 101A includes a channel 103 extending through a central section of the injection monitoring device 101A. The channel 103A can be configured to receive a portion of the syringe therethough when the injection monitoring device 101A is mated to syringe.

The injection monitoring device 101A also includes flange members 107A and 107B extending laterally from the central opening 103. The flange members 107A and 107B can be configured to act as a syringe flange when coupled to the syringe.

In some embodiments, the injection monitoring device 101A can be configured to couple to or fit over a flange of the syringe. For example, in some embodiments, the injection monitoring device 101A includes a separate top section 109 and bottom section 111 that can be placed around the flange and secured to one another to mate the injection monitoring device 101A to the syringe. In some embodiments, the injection monitoring device 101A can include a sleeve configured to extend around one or more surfaces of the flange of the syringe. While coupling of the injection monitoring device 101A to the flange of the syringe is discussed, the injection monitoring device 101A can be configured to couple to any suitable portion of the syringe using any suitable coupling mechanism. For example, fasteners, clips, or other engagement means are contemplated.

Figure 2:
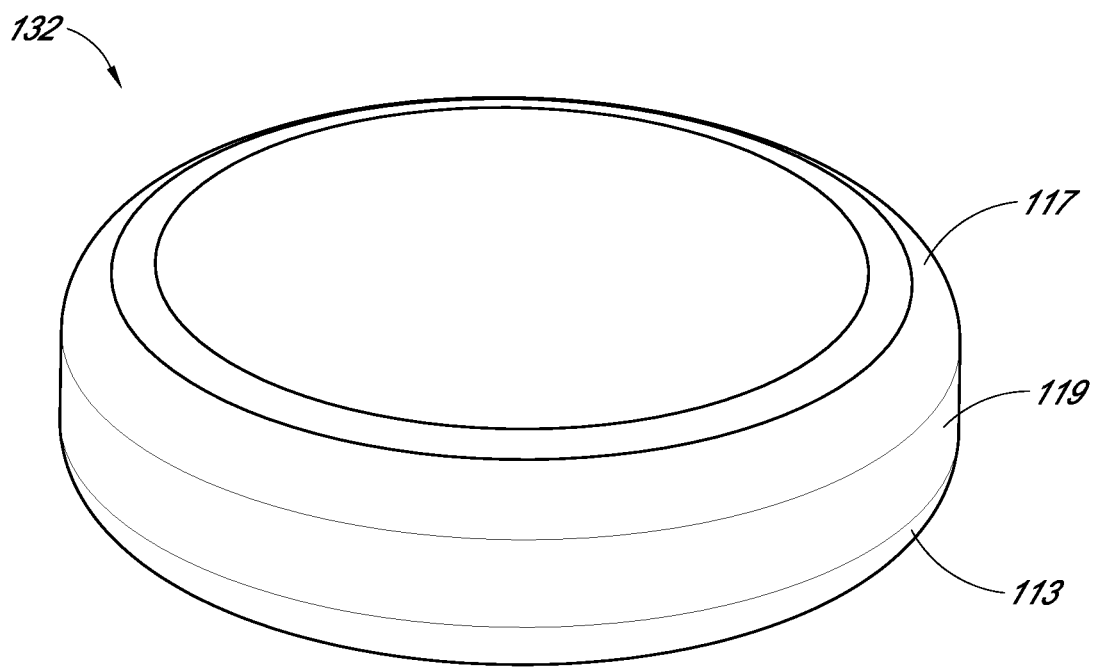
FIG. 2 depicts a perspective view of an injection monitoring device that attaches to a syringe plunger in accordance with an illustrative embodiment of the present invention.

FIG. 2 depicts an illustrative embodiment of an injection monitoring device 132 configured to mate with a syringe, such as, for example, a safety syringe. The injection monitoring device 132 can include a body 119 shaped as a cap or disk and can be configured to mate to a finger press of a plunger of a syringe. The body 119 can include a top section 117 and a bottom section 113. In some embodiments, the bottom surface 113 of the body 119 of the injection monitoring device 132 is configured to mate with a top surface of the finger press of the syringe and the top section 117 is configured to operate as a finger press of the syringe. In some embodiments, a portion of the injection monitoring device 132 is configured to extend around at least a portion of the finger press of the syringe. For example, in some embodiments, the injection monitoring device 132 can include a sleeve. In some embodiments, the injection monitoring device 132 is configured to mate with a plunger rod of the syringe. The injection monitoring device 132 can be configured to couple to the syringe using any suitable coupling means. For example, fasteners, clips, or other engagement means are contemplated.

Figure 3A:
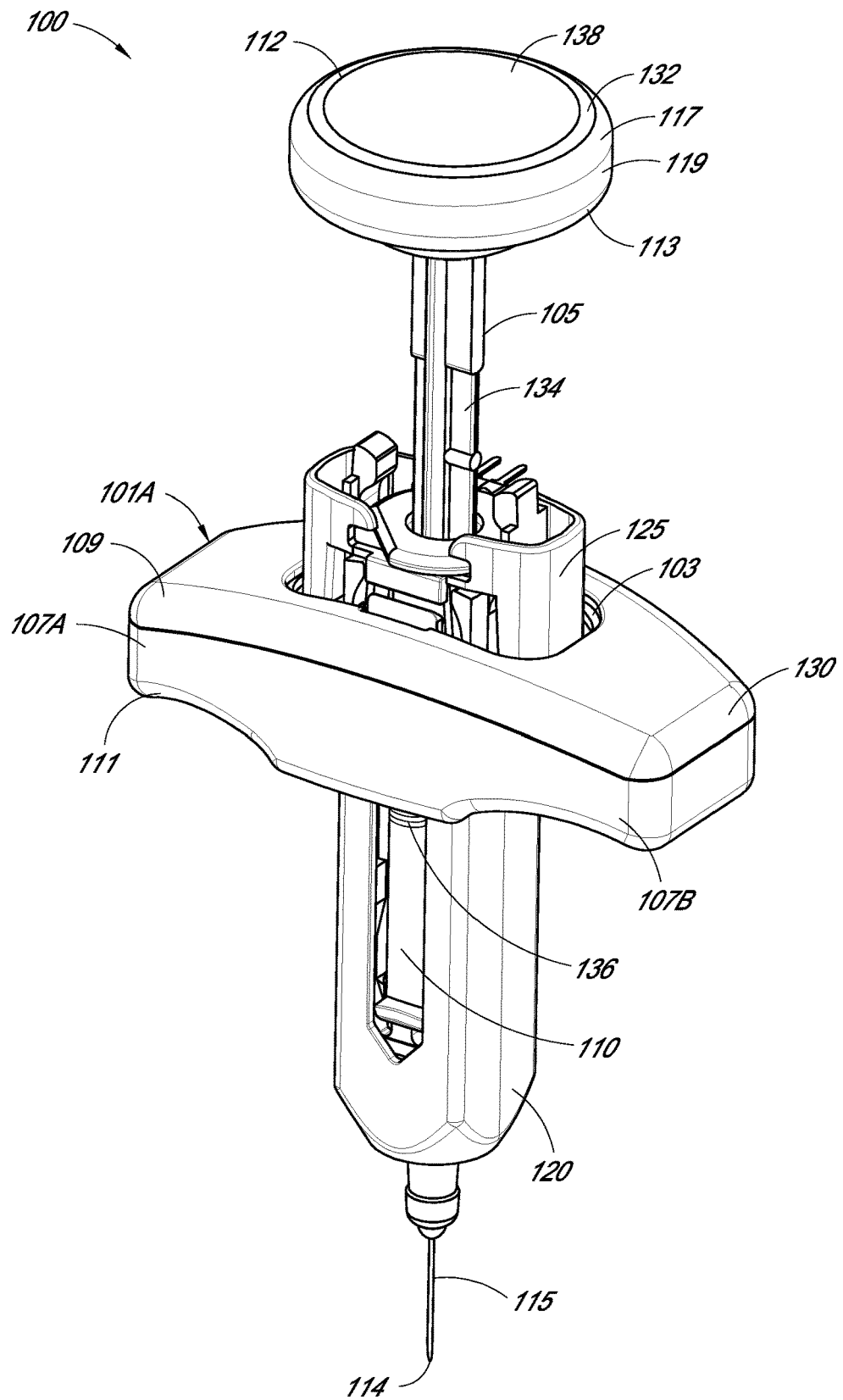
FIG. 3A depicts a side perspective view of an injection monitoring system, including injection monitoring devices connected to a safety syringe in accordance with an illustrative embodiment of the present invention.
Figure 3B:
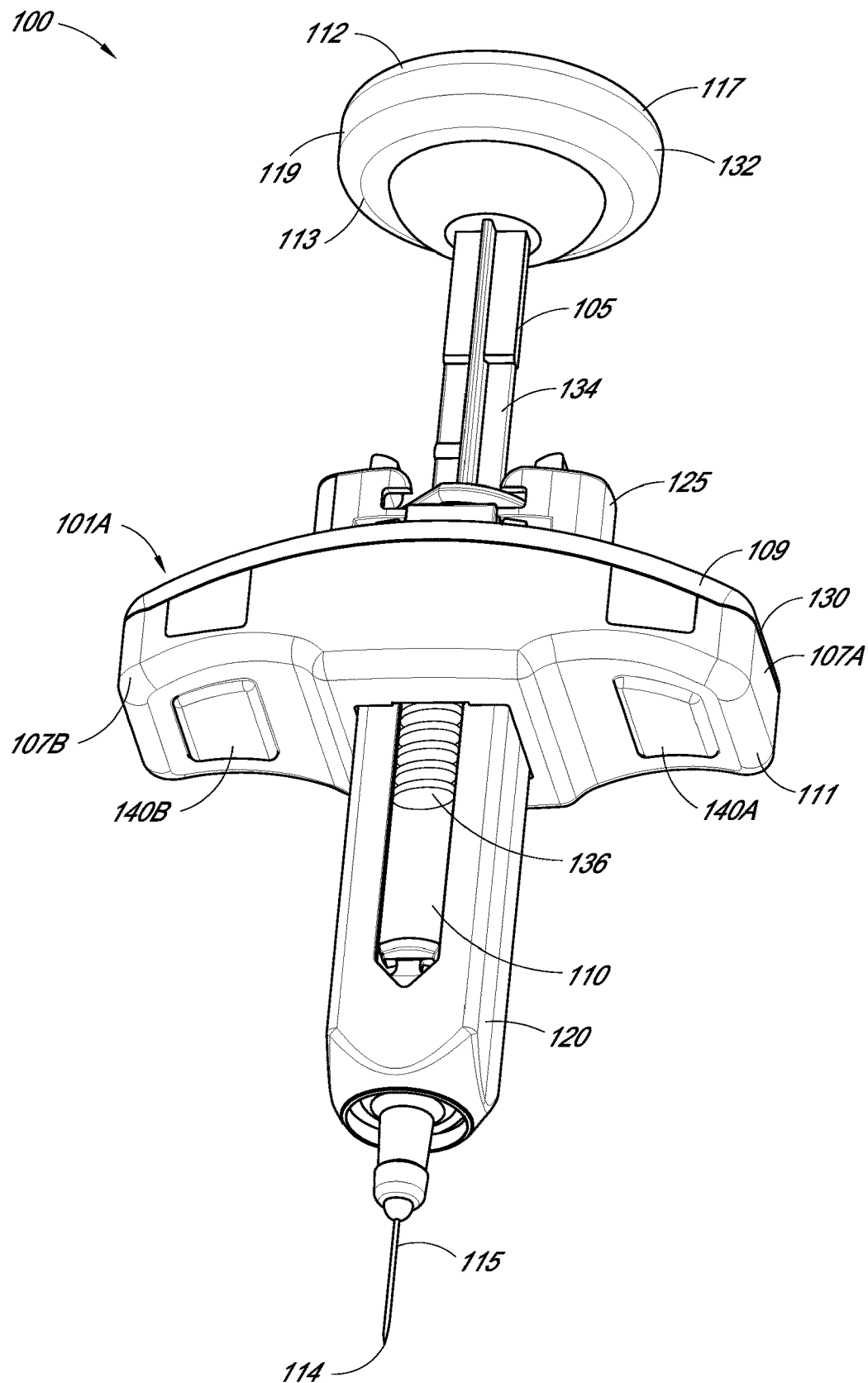
FIG. 3B depicts a lower perspective view of an injection monitoring device system including injection monitoring devices connected to a safety syringe in accordance with an illustrative embodiment of the present invention.

FIGS. 3A and 3B depict an illustrative embodiment of an injection monitoring system 100 including a syringe mounted to an injection monitoring device 101A and an injection monitoring device 132. Although both the injection monitoring device 101A and injection monitoring device 132 are shown in FIGS. 1A and 1B, it should be recognized that the dose monitoring functions described herein can be performed with only an injection monitoring device 101A mated with the syringe, with only the injection monitoring device 132 mated with the syringe, or with both the injection monitoring device 101A and the injection monitoring device 132 mated with the syringe. The syringe of the injection monitoring system 100 includes a plunger 105, a barrel 110, a needle 115, a safety shield 120, and a housing member 125.

As shown in FIG. 3A, the barrel 110, safety shield 120, and housing member 125 can extend through the central opening 103 of the injection monitoring device 101A when the injection monitoring device 101A is mated to the syringe. The injection monitoring device 101A can be positioned to function as a flange 130 of the injection monitoring system 100 when mated to the syringe, and may be referred to as the flange 130 hereinafter.

The injection monitoring device 132 can be positioned to function as a finger press 132 of the injection monitoring system 100 when mated to the syringe, and may be referred to as the finger press 132 hereinafter when discussing the injection monitoring system 100. The finger press 132 of the plunger is positioned at a proximal end 112 of the injection monitoring device and the needle 115 extends to a distal end 114 of the injection monitoring device.

The plunger 105 can include a plunger rod 134 and a stopper 136. The electronic finger press 132 can be mated to the plunger rod 134 or an existing finger press connected to the plunger rod 134. In operation, the plunger 105 can be displaced linearly into or out of the interior of the barrel 110. When the plunger 105 is displaced linearly out of the barrel 110, fluid is drawn in through the needle 115 and into the barrel 110. When the plunger 105 is displaced into the barrel 110, fluid is emitted out of the barrel 110 through the needle 115. The stopper 136 creates a seal along the sidewalls of the barrel 110 so that fluid is confined to the section of the barrel 110 between the stopper 136 and the needle 115.

In operation, the plunger 105 can be displaced linearly into the barrel 110 through manipulation of the electronic finger press 132 by a user. It is contemplated that in use of the injection monitoring system 100, a user may advance the plunger 105 into the barrel 110 by applying a force distally in the direction of the needle 115 to a sensor cover 138 of the electronic finger press 132 of the plunger 105 that can be positioned over one or more force sensors (not shown) within the electronic finger press 132 while simultaneously applying a force in the proximal direction to one or more sensor covers 140A and 140B positioned on the underside of the flange 130 that can be positioned over one or more force sensors (not shown) within the flange 130. In some embodiments, a user may apply a force to the finger press 132 with a first finger, such as a thumb. The user may apply a force to the sensor cover 140A of the flange 130 with a second finger and the sensor cover 140B of the flange 130 with a third finger. In some embodiments, the sensor cover 140A of the flange 130 and sensor cover 140B of the flange 130 are positioned on opposite sides of the barrel 110.

The sensor covering 138 of the electronic finger press 132 may be pliant or deformable surface configured to cover one or more force sensors (not shown) within the finger press 132. The one or more force sensors may be positioned in the electronic finger press 132 to detect force exerted on the exterior of the sensor covering 138. For example, the one or more force sensors positioned in the electronic finger press 132 may detect a force resulting from depression of the electronic finger press 132 by a finger of a user to linearly displace the plunger 105 into the barrel 110.

As show in FIG. 3B, the sensor covers 140A and 140B can be positioned on the underside of the flange 130. The sensor covers 140A and 140B can each cover one or more force sensors (not shown). The sensor covers 140A and 140B can include pliant or deformable surfaces covering the force sensors. The one or more force sensors positioned in the flange 130 can be configured to detect force exerted on the exterior of the surface of the flange 130. For example, the one or more force sensors positioned in the flange 130 may detect a force resulting from a user grasping and squeezing the sensor covers 140A and 140B of the flange 130 when linearly displacing the plunger 105 into the barrel 110.

In a typical injection using injection monitoring system 100, several stepwise changes in actuating force at the electronic finger press 132 and underside of the flange 130 occur. A first change in force occurs, upon initiation of an injection at which the actuating force increases from zero to a first magnitude or first range of magnitudes. When the fluid is emptied from the barrel 100, corresponding to full dose delivery, the stopper 136 bottoms out by reaching its lowest point within the barrel 110 at which a distal end of the stopper strikes a surface of the barrel 110 and is prevented from further progression distally within the barrel 110 towards the needle 115. In normal use of the injection monitoring system 100, a second change of force occurs during bottoming out of the stopper 136, which is accompanied by an increase in force exerted by the user from the first magnitude or first range of magnitudes to a second magnitude or second range of magnitudes greater than the first magnitude or first range of magnitudes. This may be due to a delay in the reaction of the user in recognizing that a full dose has been injected. A third change in force occurs when the user removes their finger(s) from the electronic finger press 132 and/or underside of the flange 130. When the user removes their finger(s) from the electronic finger press 132 and/or the underside of the flange 130, the actuating force decreases from the second magnitude or second range of magnitudes to zero. The force sensors positioned within the electronic finger press 132 and flange 130 can be positioned to detect one or more of the first change in force, second change in force, and third change in force.

Figure 4:
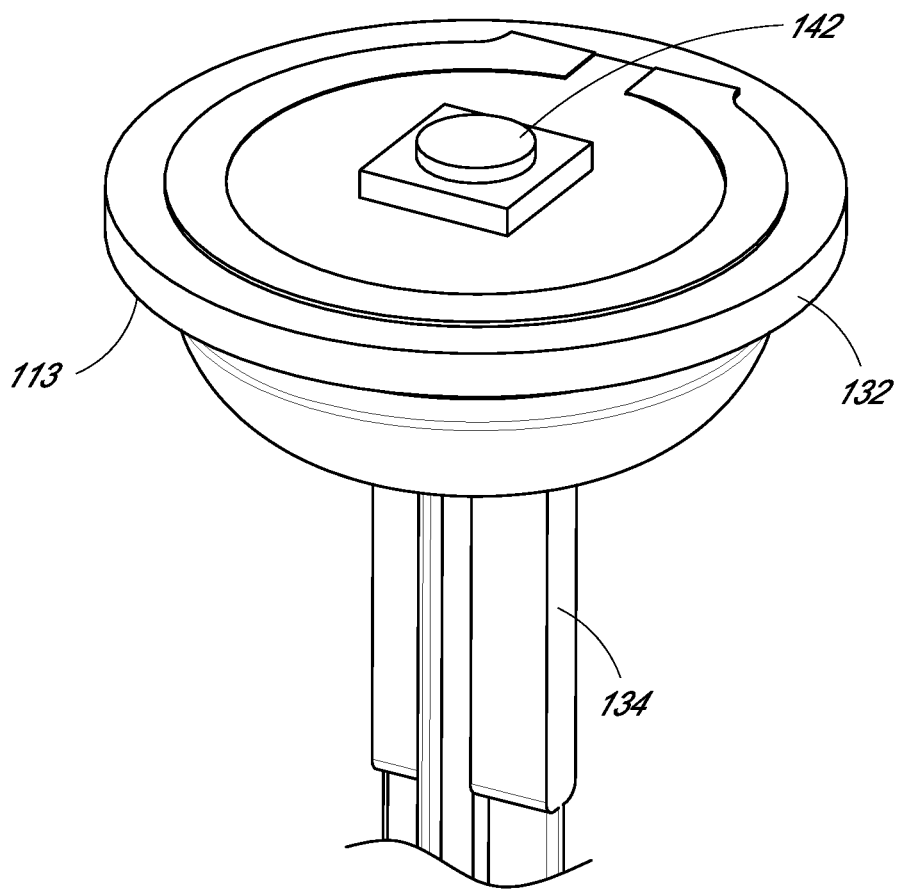
FIG. 4 depicts a sectional view of an electronic thumb press type injection monitoring device connected to a plunger of a safety syringe in accordance with an illustrative embodiment.

FIG. 4 shows the electronic finger press 132 in connection with the plunger 105 with the surface 138 removed. The injection monitoring device includes a force sensor 142. The force sensor 142 is positioned to align with the surface 138. The force sensor 142 is positioned to detect changes in force exerted on surface 138 during performance of an injection using the injection monitoring system 100.

The one or more force sensors 142 may be positioned in the electronic finger press 132 to detect force exerted on the exterior of the sensor covering 138. For example, the one or more force sensors 142 positioned in the electronic finger press 132 may detect a force resulting from depression of the electronic finger press 132 by a finger of a user to linearly displace the plunger 105 into the barrel 110. The force sensor 142 may include electronics or communication components that integrate the sensor with other injection monitoring devices attached to a syringe. Alternatively, the force sensor 142 may be connected to the top portion of the finger press 132 and be used to determine injection events, similar to the injection monitoring device that attaches to a flange of the syringe.

Figure 5:
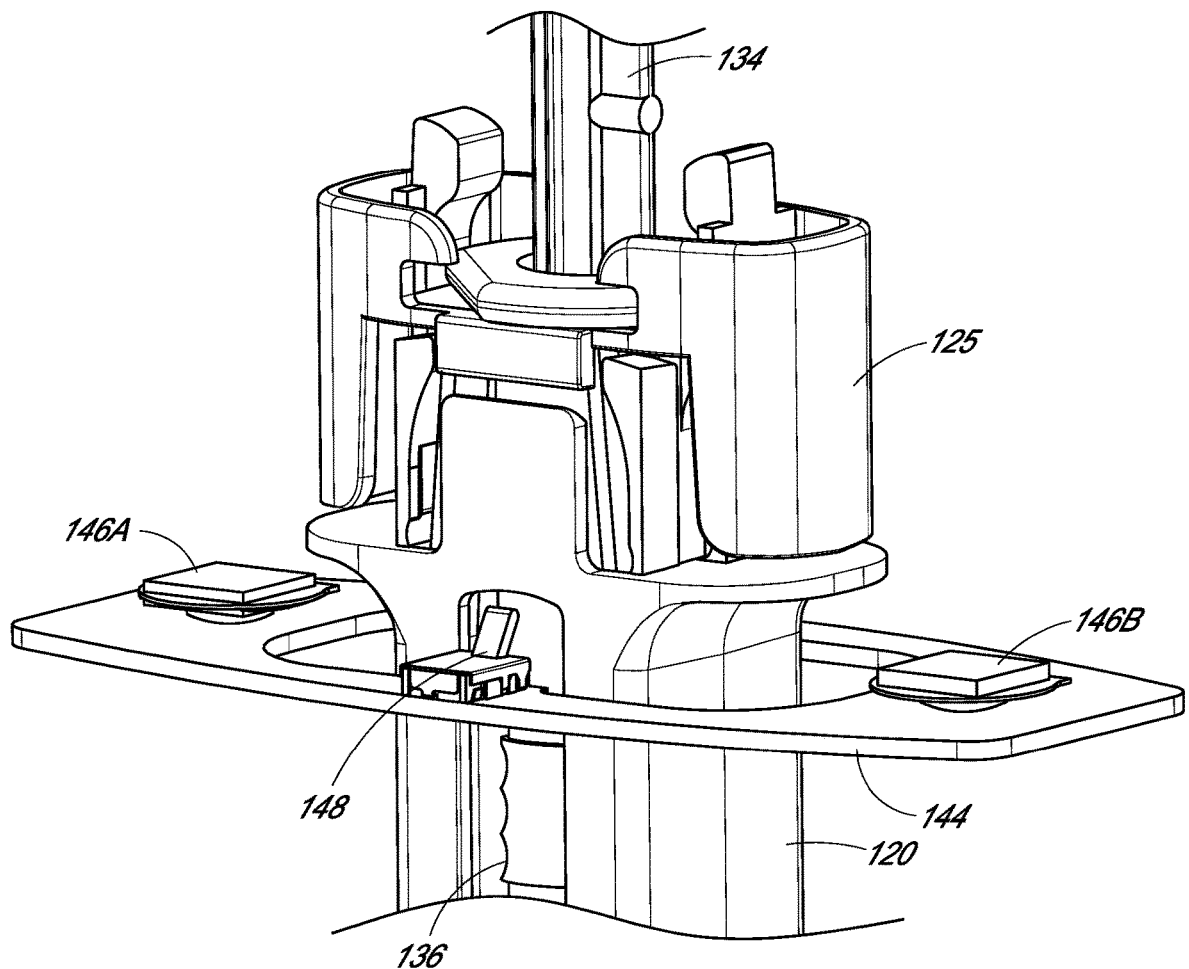
FIG. 5 depicts a sectional view of an injection monitoring system mated to a flange of a safety syringe in accordance with an illustrative embodiment.

FIG. 5 shows a section of the injection monitoring system 100 showing interior features of the flange 130. The flange 130 includes a mounting surface 19 in connection with a force sensor 146A, a force sensor 146B, and a switch 148. In some embodiments, the mounting surface 19 is a printed circuit board. The one or more force sensors 146A and 146B can be positioned in the flange 130 to detect force exerted on the exterior surface of the flange 130. For example, the force sensor 146A can be configured to align with the sensor cover 140A and to detect forces exerted on the sensor cover 140A. The force sensor 146B can be configured to align with the sensor cover 140B and detect forces exerted on the sensor cover 140B. The force sensors 142 can be positioned to detect changes in force applied to the surface 140A and the surface 140B during performance of an injection using the injection monitoring system 100. For example, the one or more force sensors positioned in the flange 130 may detect a force resulting from a user grasping and squeezing the underside of the flange 130 when linearly displacing the plunger 105 into the barrel 110. The force sensor 146A and 146B may include electronics or communication components that integrate the sensor with other injection monitoring devices attached to a syringe. Alternatively, the force sensor 146A and 146B may be connected to the underside of the flange 130 and be used to determine injection events.

The microswitch 148 can be positioned to detect deployment of the safety shield 120. In operation, performance of an injection using the injection monitoring system 100 can cause the deployment of the safety shield 120. Deployment of the safety shield 120 can refer to movement of the safety shield 120 with respect to the needle 115 so that at least a portion of the safety shield 120 extends beyond the end of the needle 115 or movement of the needle 115 into the safety shield 120 so that at least a portion of the safety shield 120 extends beyond the end of the needle 115. In some embodiments, deployment of the shield 120 includes movement of the housing member 125 in an upward direction away from the end of the needle 115. Movement of the housing member 125 causes movement of the barrel 110, plunger 105 and needle 115 in the upward direction with respect to the safety shield 120 so that the end of the needle 115 is positioned within the safety shield 120. In some embodiments, deployment of the safety shield 120 causes an initial downward movement of the safety shield 120 or housing member 125 prior to movement of the housing member 120 in the upward direction. In some embodiments, the switch 148 is positioned to be actuated by movement of the housing member 125 in the upward direction. In some embodiments, the switch 148 is positioned to be actuated by movement of the housing member 125 in the downward direction. In some embodiments, the switch 148 is positioned to be actuated by movement of the safety shield 120 in an upward direction. In some embodiments, the switch 148 is positioned to be actuated by movement of the safety shield 120 in a downward direction. In alternative embodiments, the switch 148 can be positioned to be activated by movement of one or more of the plunger 105, the barrel 110, and the needle 115. In some embodiments, the switch 148 is a microswitch.

Figure 6:
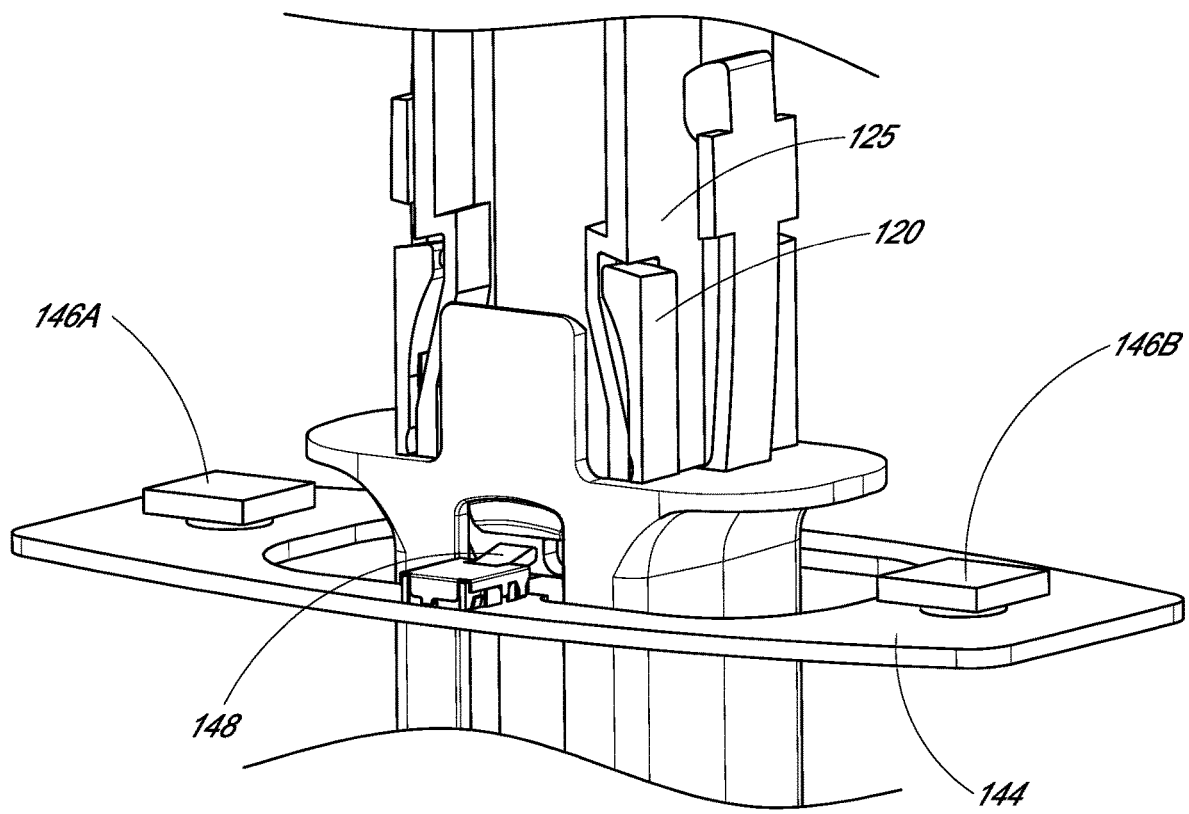
FIG. 6 depicts a sectional view of an injection monitoring system mated to a flange of a safety syringe in accordance with an illustrative embodiment.

FIG. 6 shows a section of the injection monitoring system 100 with the flange 130 removed. FIG. 6 depicts the configuration of the monitoring system 100 when the safety shield 120 is deployed. The switch 148 is shown in its activated configuration.

The injection monitoring device 101A or flange 130 may be an attachable and detachable module that can couple to a syringe or similar device to convert the syringe into an injection monitoring system. In alternative embodiments, the components of the injection monitoring device 101A or flange 130 can be integrated into the syringe itself, for example, into a flange of the syringe.

In some embodiments, the injection monitoring device comprises an electronic finger press 132 that may be an attachable or detachable module that can couple to the plunger 105. In alternative embodiments, the electronic components of the electronic finger press 132 may be integrated into the syringe itself, for example, into a finger press of the syringe.

In some embodiments, the electronic finger press 132 fits over an existing finger press of the plunger 105. The electronic finger press 132 and the sensor 142 positioned within the electronic finger press 132 can be configured to interface with multiple syringes and with syringes of different types. In some embodiments, the electronic finger press 132 can be attached to a syringe to convert the syringe into an injection monitoring device.

Figure 7:
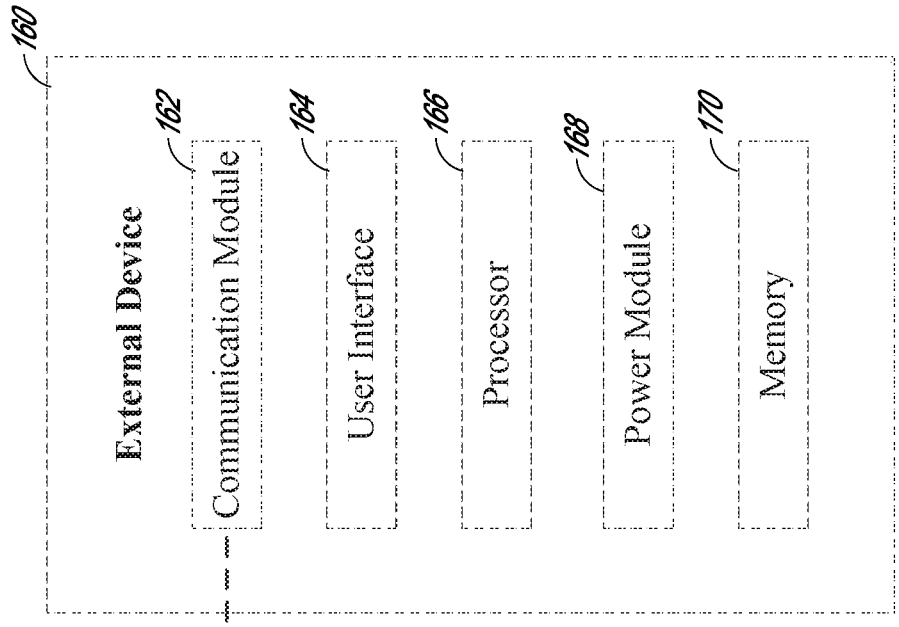
FIG. 7 is a schematic diagram of an injection monitoring device connected to an external device according to one embodiment.
Figure 7:
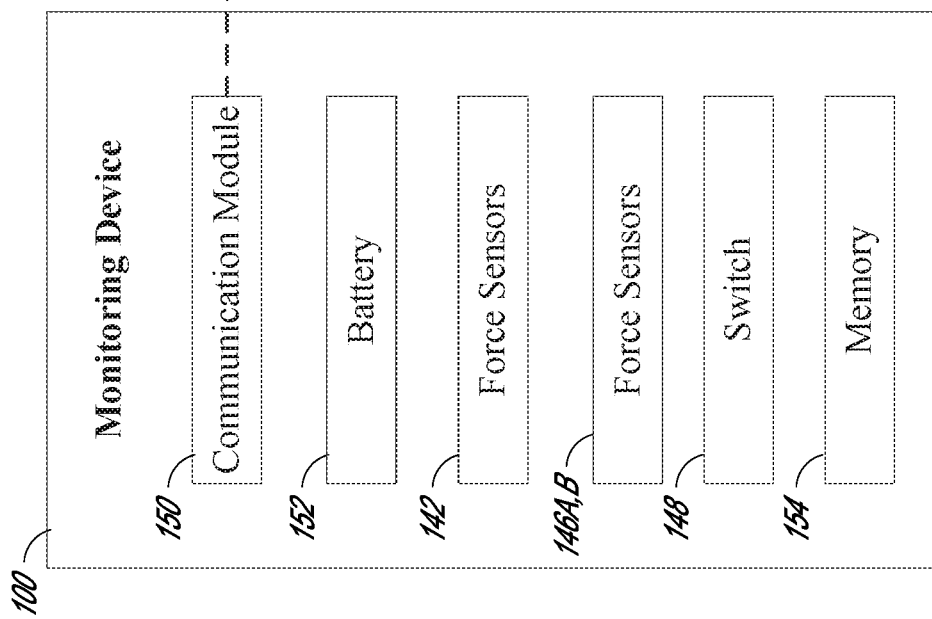

FIG. 7 depicts a schematic view of an illustrative embodiment of the injection monitoring device 101A. The dose monitoring 101A comprises a communication module 150, a battery 152, the force sensor 146A, the force sensor 146B, the switch 148, and a memory 154. While a single communication module 150, battery 152, and memory 154 are described, it is contemplated that in some embodiments, each of the injection monitoring device 101A and injection monitoring device 132 of the injection monitoring system can include or communicate with its own communication module, battery, and/or memory configured to perform the functions described herein.

In one embodiment, the communication module 150 can communicate with an external device 160 such as a mobile device, computer, server, or any other electronic external device that is known in the art. The external device 160 can include a communication module 162 for receiving data from the communication module 150. The external device 160 may also include a user interface 164 for accessing and reading data on the external device. The external device may further comprise a processor 166. The processor 166 can be configured to perform on-board processing of data received from the injection monitoring system 100 using algorithms to determine the precise time that an injection occurred and the amount of dose administered. The external device 160 may further include a power module 168 to provide power to the electrical components of the external device 160.

One or more of the force sensor 142, the force sensor 146A, and the force sensor 146B can be configure to detect and measure one or more external forces exerted on the monitoring device 100. The force sensor 142 can be configured to detect an external force exerted on the surface 138 of the electronic finger press 132. One or more of the force sensor 146A and the sensor 146B can measure external forces exerted on the surface 140A and the surface 140B, respectively, of the flange 130. The force sensor 142, the force sensor 146A, and the force sensor 146B can include any sensing technology suitable for capturing changes in force or load including, but not limited to capacitance sensing, resistance sensing, inductance sensing, and reflectivity sensing. In some embodiments, one or more of the force sensor 142, the force sensor 146A, and the force sensor 146B can produce an analog signal that correlates with a magnitude of force applied to the sensor(s).

In some embodiments, one or more of force sensor 142, the force sensor 146A, and the force sensor 146B is a two-stage switch or two-switch system. In some embodiments, a two-stage switch or two-switch system can allow for detection of a first change in force from zero to a first magnitude and a second change in force from the first magnitude to a second magnitude, the second magnitude being greater than the first magnitude. For example, in a two-stage switch or two-switch system, a first switch can be configured to close when a force above the first magnitude is applied and a second switch can be configured to close when a force above the second magnitude is applied, the second magnitude being greater than the first magnitude. Conversely, the second switch can be configured to open when the force applied to the injection monitoring system 100 decreases below the second magnitude, and the first switch can be configured to open when the force applied to the injection monitoring system 100 decreases below the first magnitude.

The battery 152 can be configured to supply power to the electrical components of the injection monitoring system 100. The battery 152 may be rechargeable. The battery 152 may also include an external switch. In one embodiment, the injection monitoring system 100 can be configured so that one or more of the force sensor 142, the force sensor 146A, the force sensor 146B, and the switch 148 are activated at any time that the battery 152 is supplying power to the injection monitoring system 100.

The memory 154 can be configured to store data from one or more of the force sensor 142, the force sensor 146A, the force sensor 146B, and the switch 148. The memory 154 may comprises a data storage device such as a flash drive or memory card. In alternative embodiments, the injection monitoring system 100 can be configured to engage such a data storage device in order to transmit data to the external device 160.

The communication module 150 can be configured to allow the transmission of data to the external device 160. The communication module 150 can be connected to the external device 160 through a wired or wireless connection. The communication module 150 can be configured to perform short-distance RF communication, such as Bluetooth, BLE, or ZigBee®. The injection monitoring system 100 can further comprise one or more ports or slots to allow for a wired connection between the injection monitoring system 100 and an external device. For example, the injection monitoring system 100 can include a port or slot positioned to facilitate a wired connection to one or more of the force sensor 142, the force sensor 146A, the force sensor 146B, and the switch 148. Data from the injection monitoring system can be transmitted to one or more of the patient, clinician, payor, pharmacy, and or authorized receivers, for example, to provide information regarding adherence to a treatment regimen.

As described herein, one or more of the force sensor 142, the force sensor 146A, and the force sensor 146B can detect and/or measure force exerted on the electronic finger press 132 of the plunger 105 of the syringe and/or the underside of the flange 130. In an illustrative embodiment, the processor 166 can be configured to process the data streams supplied by one or more of the force sensor 142, the force sensor 146A, and the force sensor 146B to determine which applications of force on the injection monitoring system 100 are associated with an injection event. For example, in embodiments in which an analog signal is provided by the force sensor 142, force sensor 146A, and force sensor 146B, the processor 166 can be configured to analyze the analog signal to determine the occurrence of one or more injection events, such as initiation of an injection, end of injection, shield deployment, and/or release of the plunger 105 by the user. The analog signal can be analyzed for a change in applied force from zero to a first magnitude or range of magnitudes to determine initiation of an injection. The analog signal can be analyzed for a change in applied force from the first magnitude or first range of magnitudes to a second magnitude or second range of magnitudes greater than the first magnitude or first range of magnitudes to determine end of injection. The analog signal can be analyzed for a change in applied force from the second magnitude or second range of magnitudes to zero to determine release of the plunger 105 and/or flange 130 by the user. In some embodiments, deployment of the safety shield 120 can result in a momentary and relatively small increase in the force measurements produced by the force sensors while the applied force decreases from the second magnitude or second range of magnitudes to zero. The processor can analyze the analog signal for an increase in magnitude between two periods of periods of decreasing magnitude to determine deployment of the safety shield 120.

In embodiments in which one or more of the force sensor 142, the force sensor 146A, and the force sensor 146B is a two-stage switch or two-switch system, the processor can determine initiation of an injection when closure of the first switch is detected. The processor can determine completion of injection when closure of the second switch is detected. The processor can also determine release of the plunger 105 and/or flange when the second switch and first switch open after being closed.

In some embodiments, the data streams supplied by the force sensor 142, the force sensor 146A, and/or the force sensor 146B can be correlated with time information provided by a timer within the injection monitoring system 100 or the external device 160. The timer can be configured to record a time at each instance that the force sensor 142, the force sensor 146A, and/or the force sensor 146B obtain data so that each set of data has an associated time. In some embodiments, the timer can comprise a digital clock. The processor can be configured to process the data streams supplied by one or more of the force sensor 142, the force sensor 146A, the force sensor 146B, and the timer to determine at what time an injection event occurred, and the time over which the injection event occurred. In some embodiments, one or both of the injection monitoring device 101A and injection monitoring device 132 can include a timer.

The processor 146 can further be configured to perform calculations using the data streams supplied by one or more of the force sensor 142, the force sensor 146A, and the force sensor 146B during injection to determine the amount of dose expelled from the syringe during injection. The calculated amount of dose and the time data associated with the injection event can be recorded to the memory 170 and displayed on a user interface 164.

In some embodiments, the injection monitoring system 100 can include an orientation sensor such as an accelerometer. The orientation sensor can be configured to determine the orientation of the injection monitoring system 100. In some embodiments, the orientation sensor is further configured to detect sudden motions of the injection monitoring system 100, such as, for example, those that may occur when a user taps on the injection monitoring system 100 during a priming of the injection monitoring system 100. The orientation sensor may comprise a single-axis accelerometer or a multiple-axis accelerometer. In some embodiments, data from the accelerometer can be correlated with data from one or more of the force sensor 142, the force sensor 146A, the force sensor 146B, and the timer. In some embodiments, one or both of the injection monitoring device 101A and injection monitoring device 132 can include an orientation sensor.

In some embodiments, data from the orientation sensor can be processed to determine which exertions of pressure on the injection monitoring system 100 correspond to injection events. For example, the processor 166 may be configured to reject data recorded when it is detected that an external load is being applied to one or more of the force sensor 142, the force sensor 146A, and force sensor 146B, but the detected orientation of the injection monitoring system 100 is such that the needle 115 is pointed upwards above a certain angle. Furthermore, the processor may be configured to reject data recorded when it is detected that an external load is being applied to one or more of the force sensor 142, the force sensor 146A, and the force sensor 146B, but a sudden motion is detected to have occurred the application of the external load, such as tapping of the injection monitoring system 100 as may occur during priming. In contrast, the processor 166 can be configured to accept sensor data if it is detected in the most recent exertion of force on one or more of the force sensor 142, the force sensor 146A, and the force sensor 146B, that the orientation of the injection monitoring system 100 was generally so that the needle 115 was pointed downward below a certain angle, and that there were no sudden syringe motions associated with the application of force. These conditions are likely to be present in the event of an actual injection.

As described above, switch 148 can detect deployment of the safety shield 120. The switch 148 can be an electrical switch. In some embodiments, the switch 148 is a microswitch. Although a switch is described herein, detection of deployment of the safety shield can be performed by any suitable sensor technology including, but not limited to, capacitive sensors, inductive sensors, magnetic sensors, and optical sensors. In an illustrative embodiment, the processor 166 can be configured to process the data streams supplied by the switch 148 to determine the occurrence of one or more injection events or to identify a state of the injection monitoring device. In some embodiments, the processor 166 can be configured to process data streams supplied by the switch 148 to determine dose completion. For example, in some embodiments, safety shield deployment is contingent on delivery of a full dose. In such embodiments, data from the switch 148 indicating safety shield deployment can be interpreted by the processor 166 to indicate dose completion.

In some embodiments, the data streams supplied by the switch 148 can be correlated with time information provided by a timer within the injection monitoring system 100 or the external device 160. The timer can be configured to record a time at each instance that the switch 148 obtains data so that each set of data has an associated time. The processor 166 can be configured to process the data streams supplied by the switch 148 and the timer to determine at what time an injection event occurred.

It should be recognized that a user may connect the injection monitoring system 100 to the external device 160 after multiple dose administrations. The processer 166 can be configured to accept data for more than one recorded exertion of force on the injection monitoring system 100 during each connection to the injection monitoring system 100.

The user interface 164 can be configured to allow a user to access the amount of dose data and/or time data recorded in the memory 170. A user may access this data to determine an amount of dose and/or time for their next injection. The user interface 164 may comprise a touch screen, a keyboard and display screen, or any other user interface known in the art.

In one embodiment, the memory 170 is configured to retain data for a defined number of the most recent injections. In an alternative embodiment, the memory 170 may be configured to retain data for only the most recent recorded injection.

Figure 8:
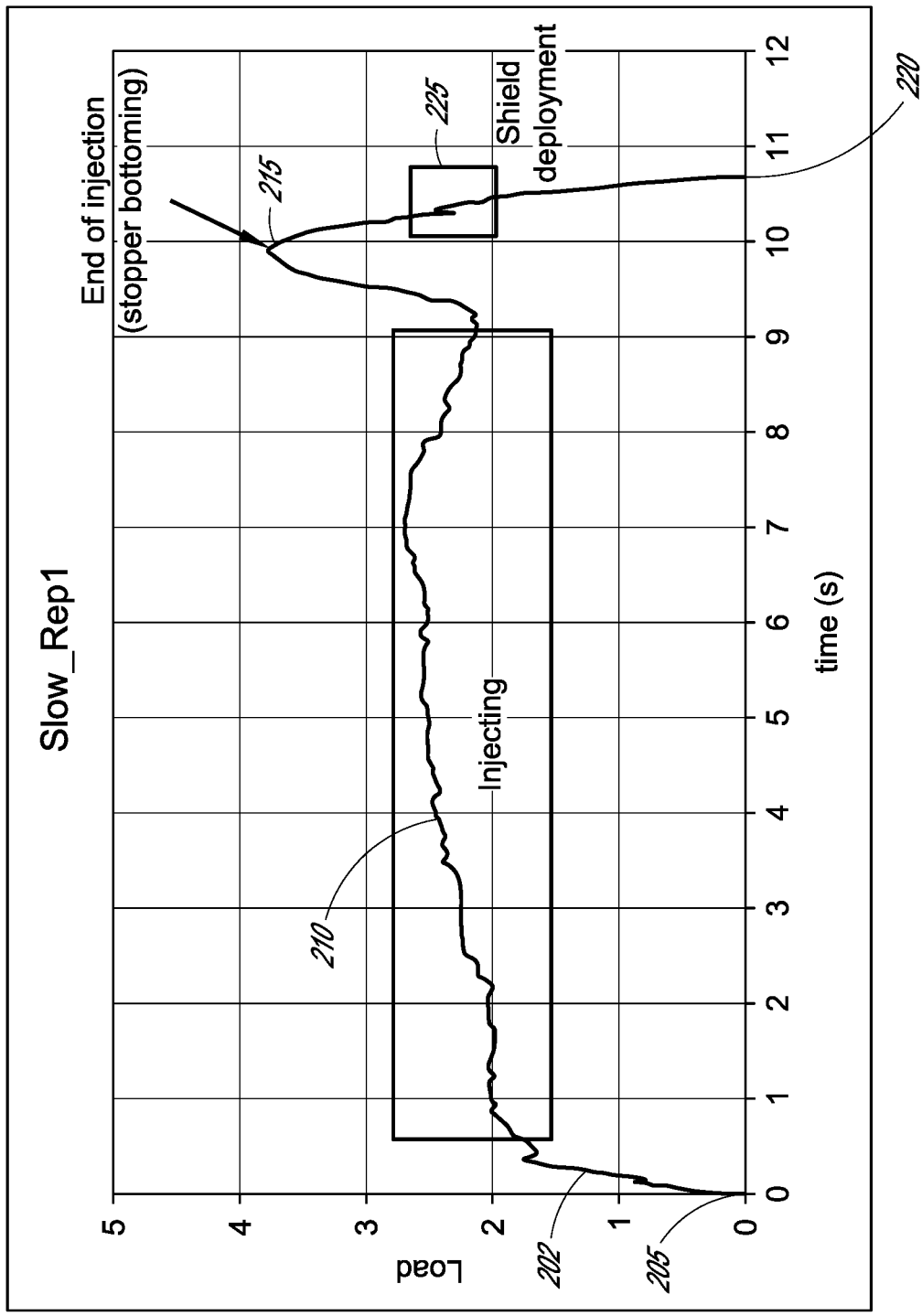
FIG. 8 depicts an example of an analog sensor trace in accordance with an illustrative embodiment.

The injection monitoring system 100 can further include one or more motion sensors, identification sensors, temperature sensors, timers, or any other suitable sensors for detecting injection related data or a state of the injection monitoring device. In some embodiments one or both of the injection monitoring device 101A and injection monitoring device 132 can include one or more motion sensors, identification sensors, temperature sensors, timers, or any other suitable sensors for detecting injection related data or a state of the injection monitoring device. In some embodiments, the injection monitoring system 100 can be configured to capture, store, and/or transmit data related to device identification, timestamp information, temperature, physical integrity, dose activation, dose progression, dose completion, and safety shield deployment. In some embodiments, the injection monitoring system 100 can be a dose monitoring system. In some embodiments, one or both of the injection monitoring device 101A and injection monitoring device 132 can be configured to capture, store, and/or transmit data related to device identification, timestamp information, temperature, physical integrity, dose activation, dose progression, dose completion, and safety shield deployment. In some embodiments, one or both of the injection monitoring device 101A and the injection monitoring device 132 can be an injection monitoring device FIG. 8 depicts an illustrative embodiment of an analog sensor trace 200 of a force sensor of an injection monitoring device, such as injection monitoring device 101A or injection monitoring device 132, connected to a syringe, for example, as described with respect to the injection monitoring system 100. The analog sensor trace 200 shows a signal 202. The analog sensor trace 200 shows load measurements on the y-axis and time measurements on the x-axis. The analog signal 202 shown in FIG. 8 is a voltage signal from a sensor in which the voltage is proportional to the applied load. In alternative embodiments, the load measurements on the y-axis may be relative measurements based on capacitance, resistance, inductance, reflectivity, or any other measurable property that can be correlated with or proportional to an applied load. The signal 202 includes a point 205 indicative of the load before initiation of an injection. At point 205, the load is at zero. The signal 202 also includes a segment 210 indicative of an injection in process. As shown in segment 210 the load has increased from zero and is within a first range of magnitude indicating a relatively steady administration of force to the force sensors of the injection monitoring device. The signal 202 further includes a point 215 at a maximum of the signal 202. The point 215 is positioned after an increase from the first range of magnitude represented by segment 210 and can be interpreted to represent completion of injection as described herein. As shown in FIG. 8, there is an increase in magnitude from the segment 210 to the point 215. The signal 202 further shows a point 220 occurring after the point 215. At the point 220, the magnitude of the load is at zero. The detected magnitude decreases between the point 215 and the point 220, which can be interpreted as being indicative of release of a plunger and/or flange of the injection monitoring device by a user. The signal 202 further includes a region 225. In the region 225, there is a relatively small increase in force at a time between the point 215 and the point 220 over which the detected magnitude is generally decreasing. In some embodiments, the detected increase in force in region 225 can be determined to indicate deployment of a safety shield.

Determination of injection events or changes in injection state can be determined using any suitable signal processing techniques for determining changes in the signal from the force sensors. In some embodiments, thresholding may be used. For example, in some embodiments, a determination of an end of injection can occur when a change is detected from a steady load, a load without any changes in magnitude beyond a range of tolerance, occurring over a duration of longer than an expected injection time, for example, region 210, to a load that is noticeably or detectably higher by a more than a predetermined magnitude in comparison to the steady load. In some embodiments, a determination of end of injection only occurs if the duration of the higher load is of less than a predetermined duration of time, for example, a few seconds. In some embodiments, the determination of end of injection only occurs if a drop in the magnitude of the load to zero occurs within a predetermined duration of time, for example, a few milliseconds from the end of the peak load.

In some embodiments, signal processing can be used to determine the instantaneous and/or total dose delivered from the injection monitoring device. For example, delivered volume can be approximated by determining the area under the curve for the signal 200 and comparing the result to that of a reference value. For a known fluid, assuming a narrow variability of losses due to frictional and visco-elastic forces from the plunger components and flow path, the total force exerted to inject the fluid will be directly proportional to the amount of the injected fluid. For example, if an injection is performed using a 1 ml Neopak™ syringe filled with a drug, the load*time area under the curve of the analog signal can be used to approximate a delivered volume of the drug using the calculation:

$$V = 1\text{ ml} * \frac{AUC}{AUC_{ref}}$$

V is the delivered volume of the drug. AUC is the calculated area under the curve. $AUC_{ref}$ is the calculated reference value.

The signal 202 is representative of a signal produced by force sensors, such as force sensor 142, force sensor 146A, and force sensor 146B, of an injection monitoring device, such as injection monitoring device 101A or injection monitoring device 132, in connection with a syringe, as described herein with respect to injection monitoring system 100. However, one of skill in the art would recognize that the signal produced during an injection may differ from that shown in trace 200 due to a variety of factors including behavior of a user, the type of medicament in the injection monitoring device, and the type of force sensor within the injection monitoring device. The signal processing techniques described herein may be applicable to any signals generated by a force sensor of an injection monitoring device.

Implementations disclosed herein provide systems, methods and apparatus for monitoring dosing data of a syringe. One skilled in the art will recognize that these embodiments may be implemented in hardware, software, firmware, or any combination thereof.

The functions described herein may be stored as one or more instructions on a processor-readable or computer-readable medium. The term "computer-readable medium" refers to any available medium that can be accessed by a computer or processor. By way of example, and not limitation, such a medium may comprise RAM, ROM, EEPROM, flash memory, CD-ROM or other optical disk storage, magnetic disk storage or other magnetic storage devices, or any other medium that can be used to store desired program code in the form of instructions or data structures and that can be accessed by a computer. Disk and disc, as used herein, includes compact disc (CD), laser disc, optical disc, digital versatile disc (DVD), floppy disk and Blu-ray® disc where disks usually reproduce data magnetically, while discs reproduce data optically with lasers. It should be noted that a computer-readable medium may be tangible and non-transitory. The term "computer-program product" refers to a computing device or processor in combination with code or instructions (e.g., a "program") that may be executed, processed or computed by the computing device or processor. As used herein, the term "code" may refer to software, instructions, code or data that is/are executable by a computing device or processor.

Software or instructions may also be transmitted over a transmission medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of transmission medium.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component or directly connected to the second component. As used herein, the term "plurality" denotes two or more. For example, a plurality of components indicates two or more components.

The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

In the foregoing description, specific details are given to provide a thorough understanding of the examples. However, it will be understood by one of ordinary skill in the art that the examples may be practiced without these specific details. For example, electrical components/devices may be shown in block diagrams in order not to obscure the examples in unnecessary detail. In other instances, such components, other structures and techniques may be shown in detail to further explain the examples.

Headings are included herein for reference and to aid in locating various sections. These headings are not intended to limit the scope of the concepts described with respect thereto. Such concepts may have applicability throughout the entire specification.

It is also noted that the examples may be described as a process, which is depicted as a flowchart, a flow diagram, a finite state diagram, a structure diagram, or a block diagram. Although a flowchart may describe the operations as a sequential process, many of the operations can be performed in parallel, or concurrently, and the process can be repeated. In addition, the order of the operations may be re-arranged. A process is terminated when its operations are completed. A process may correspond to a method, a function, a procedure, a subroutine, a subprogram, etc. When a process corresponds to a software function, its termination corresponds to a return of the function to the calling function or the main function.

The previous description of the disclosed implementations is provided to enable any person skilled in the art to make or use the present invention. Various modifications to these implementations will be readily apparent to those skilled in the art, and the generic principles defined herein may be applied to other implementations without departing from the spirit or scope of the invention. Thus, the present invention is not intended to be limited to the implementations shown herein but is to be accorded the widest scope consistent with the principles and novel features disclosed herein.

What is claimed is:

1. A method for monitoring progress of an injection of a medicament, comprising:

providing a syringe configured to administer the medicament and an injection monitoring device, the injection monitoring device comprising:

one or more flange members configured to fit over a flange of the syringe so that at least a portion of the flange of the syringe is positioned A) within each of the one or more flange members, B) beneath a top section of each of the one or more flange members, and C) above a bottom section of each of the one or more flange members, the one or more flange members being configured to be gripped during performance of an injection, wherein the one or more flange members comprises a first flange member and a second flange member; and a pair of force sensors positioned within an underside of the one of the one or more flange members on a mounting surface within an interior of the one or more flange members and configured to detect upwards pressure by a pair of fingers during performance of an injection, wherein the pair of force sensors comprises:

a first force sensor positioned within the first flange member, wherein the first force sensor is positioned to detect upward pressure by a first finger of the pair of fingers during performance of the injection; and a second force sensor positioned within the second flange member, wherein the second force sensor is positioned to detect upward pressure by a second finger of the pair of fingers during performance of the injection;

wherein the first flange member comprises a first pliant sensor cover positioned on the underside of the first flange member and aligned with the first force sensor, wherein the first pliant sensor cover is configured to be pressed by the first finger, and wherein the second flange member comprises a second pliant sensor cover positioned on the underside of the second flange member and aligned with the second force sensor, wherein the second pliant sensor cover is configured to be pressed by the second finger;

detecting data from the pair of force sensors; and determining a state of the syringe based at least in part on the detected data.

2. The method of claim 1, further comprising a second injection monitoring device configured to mate with a proximal end of a plunger of the syringe.

3. The method of claim 1, wherein the injection monitoring device comprises a channel configured to receive at least a portion of the syringe, wherein the first flange member and the second flange member extend laterally from the channel and are positioned on opposite sides of the channel.

4. The method of claim 1, wherein determining a state of the syringe comprises determining one or more of dose activation, dose progression, and dose completion.

5. The method of claim 1, further comprising determining an amount of medicament injected by the syringe based at least in part on the detected data.

6. The method of claim 1, wherein the pair of force sensors are configured to produce an analog signal correlated with a magnitude of force applied to the pair of force sensors, wherein the method further comprises analyzing the analog signal and determining an amount of medicament injected by the syringe based at least in part on an area beneath the analog signal.

7. The method of claim 1, wherein the pair of force sensors comprise two-stage switches or analog sensors.

8. The method of claim 1, wherein the pair of force sensors are configured to measure one or more of capacitance, resistance, inductance, reflectivity, and voltage.

9. An electronic injection monitoring device configured to mate with a syringe having a flange, comprising:

a channel configured to receive at least a portion of the syringe;

one or more flange members configured to fit over the flange of the syringe so that at least a portion of the flange of the syringe is positioned A) within each of the one or more flange members, B) beneath a top section of each of the one or more flange members, and C) above a bottom section of each of the one or more flange members, the one or more flange members being configured to be gripped during performance of an injection, wherein the one or more flange members comprises a first flange member and a second flange member;

a pair of force sensors positioned within an underside of the one or more flange members on a mounting surface within an interior of the one or more flange members and configured to detect upwards pressure by a pair of fingers during performance of an injection, wherein the pair of force sensors comprises:

a first force sensor positioned within the first flange member, wherein the first force sensor is positioned to detect upward pressure by a first finger of the pair of fingers during performance of the injection; and a second force sensor positioned within the second flange member, wherein the second force sensor is positioned to detect upward pressure by a second finger of the pair of fingers during performance of the injection; and a communication module configured to transmit data from the pair of force sensors to an external device;

wherein the first flange member comprises a first pliant sensor cover positioned on the underside of the first flange member and aligned with the first force sensor, wherein the first pliant sensor cover is configured to be pressed by the first finger, and wherein the second flange member comprises a second pliant sensor cover positioned on the underside of the second flange member and aligned with the second force sensor, wherein the second pliant sensor cover is configured to be pressed by the second finger.

10. The electronic injection monitoring device of claim 9, wherein the pair of force sensors comprise two-stage switches or analog sensors.

11. The electronic injection monitoring device of claim 9, wherein the pair of force sensors are configured to measure one or more of capacitance, resistance, inductance, reflectivity, and voltage.

12. The electronic injection monitoring device of claim 9, further comprising a sensor configured to detect deployment of a safety shield of the syringe.

13. The electronic injection monitoring device of claim 12, wherein the sensor is a switch configured to activate in response to movement of a housing member of the syringe during deployment of the safety shield.

14. The electronic injection monitoring device of claim 12, wherein the sensor configured to detect deployment of the safety shield is one of the pair of force sensors.

15. The electronic injection monitoring device of claim 9, further comprising one or more orientation sensors.

16. The electronic injection monitoring device of claim 9, further comprising a temperature sensor.

17. The electronic injection monitoring device of claim 9, wherein the syringe comprises a barrel configured to contain a medicament and a plunger configured to be displaced linearly into the interior of the barrel to dispense the medicament, the plunger comprising:
- a finger press;
- a stopper; and
- a plunger rod extending between the finger press and the stopper.

18. The electronic injection monitoring device of claim 9, wherein the injection monitoring device comprises a top piece and a bottom piece configured to secure to one another to mate the injection monitoring device with the syringe.

19. The electronic injection monitoring device of claim 9, wherein the first flange member and the second flange member extend laterally from the channel and are positioned on opposite sides of the channel.

20. The electronic injection monitoring device of claim 9, wherein the pair of force sensors are configured to produce an analog signal correlated with a magnitude of force applied to the pair of force sensors, wherein the electronic injection monitoring device further comprises a processor configured to analyze the analog signal and determine an amount of medicament injected by the syringe based at least in part on an area beneath the analog signal.

21. The electronic injection monitoring device of claim 9, further comprising a processor configured to read data from the pair of force sensors and determine a state of the syringe.

22. The electronic injection monitoring device of claim 21, wherein the processor is configured to determine one or more of dose activation, dose progression, and dose completion based at least in part on the data from the pair of force sensors.

23. The electronic injection monitoring device of claim 21, wherein the processor is configured to determine an amount of medicament injected by the syringe based at least in part on the data from the pair of force sensors.

24. The electronic injection monitoring device of claim 21, wherein the processor is configured to determine deployment of a safety shield of the syringe based at least in part on the data from the pair of force sensors.

* * * * *